United States Patent [19]

Barberet et al.

[11] Patent Number: Plant 7,181

[45] Date of Patent: Mar. 6, 1990

[54] CARNATION NAMED LONRANEG

[75] Inventors: Nicole Barberet; Henri Blanc, both of Antibes; Antonio Di Giorgio; Renato Di Giorgio, both of San Remo, all of Italy

[73] Assignee: Establissements Barberet et Blanc, La Londe-Les-Maures, France

[21] Appl. No.: 315,541

[22] Filed: Feb. 27, 1989

[51] Int. Cl.[4] ..... A01H 5/00

[52] U.S. Cl. ..... Plt./70

[58] Field of Search ..... Plt./70

*Primary Examiner*—James R. Feyrer

*Attorney, Agent, or Firm*—Charles W. Rummler

[57] ABSTRACT

A new and distinct standard carnation cultivar particularly distinguished by its medium sized blooms of a light yellow coloration, the petals of which are longitudinally and closely striated with thin lines of light pink and sometimes white, the blooms being produced profusely during the Spring, Summer and Fall flowering seasons of a plant having a recurrent blooming habit. The flowers are borne singly on long, strong, upright stems of a vigorous plant which reaches an average height of about 140 cm., at eight months of growth.

1 Drawing Sheet

BACKGROUND OF THE NEW PLANT

This new carnation cultivar originated as a seedling of a hybrid developed by us in 1985 at the San Remo, Italy nursery of Antonio and Renato Di Giorgio by crossing two varieties of carnations selected from the Di Giorgio collection of carnations maintained at their nursery for breeding purposes. This particular seedling was selected for propagation because of its very light yellow flowers variegated by each of the flower petals having light pink longitudinal striations, the flowers appearing profusely on long, strong, upright stems of a tall plant reaching a height of about 140 cm. The selected variety was propagated by us at San Remo, Italy by means of cuttings with such satisfactory results that it was decided to continue propagation of this new plant at the San Remo nursery through several successive generations by cuttings to prove that the novel characteristics of the selected seedling would be retained from generation to generation and that its homogeneity could be assured for commercial scale production.

This new carnation variety is now being propagated for cut flower production by means of cuttings, as well as in vitro propagation procedures, at Establissements Barberet et Blanc, Laboratoire de Physiologie Vegetale, 83250 La Londe-Les Maures, France.

DESCRIPTION OF THE DRAWING

Our new standard carnation cultivar is illustrated by the accompanying photographic drawing which show a bud and several flowers in various stages of development, the color rendition being as nearly true to that herein specified as is reasonably possible to obtain by professional photographic procedures.

DESCRIPTION OF THE NEW PLANT

The following is a detailed description of our new carnation variety based upon observations of plants grown in greenhouse, as well as outside, in the Spring of 1988 at San Remo, Italy, the color designations stated herein being according to The R.H.S. Colour Chart published by The Royal Horticultural Society of London, England.

THE PLANT

Origin: Seedling.

Parentage:

*Seed parent.*—Variety No. 417.

*Pollen parent.*—Variety No. 647.

Both varieties are unnamed and unpatented and are identical in the breeding records maintained at the Di Giorgio nursery office at Via Villetta 41, 18038 San Remo, Italy.

Classification:

*Botanic.*—*Dianthus caryophyllus.*

*Commercial.*—Standard Carnation.

Form: A tall, erect bush having at least four stems emitted near the ground.

Height: Averages about 140 cm. at eight months of growth.

Main stem length: Less than 15 cm. due to pinching the stem to promote growth of branches.

Branching: This plant is well branched.

Growth: Upright, vigorous and rigid.

Foliage:

*Quantity.*—Moderately abundant.

*Number of leaves.*—More than 120.

*Leaf size.*—(At the seventh node) About 10.7 cm. long and 1.1 cm. wide.

*Leaf shape.*—Oblong — With entire margin and downwardly curled.

*Texture.*—Leathery.

*Color.*—Both upper and under sides, 189-A/B.

THE BUD

Size: Medium.

*Diameter.*—Averages about 2.2 cm.

*Length.*—Averages about 3.1 cm.

Shape: Spherical, before sepals divide.

Rate of opening: Normal.

Color of petals: When sepals first divide, and petals begin to unfurl, the same as at full bloom.

Sepals:

*Number.*—Five or six.

*Shape.*—Generally ovate, with acuminate tips and joined together at their lower parts.

*Character.*—The sepals are hooded over the bud before they divide and stand up as the flower opens.

*Color.*—Inside, 145-D. Outside, 137-D and 144-D.

*Striae.*—Longitudinal.

Calyx:

*Shape.*—Bell-shaped.

*Size.*—Large.

*Aspect.*—Smooth.

*Splitting.*—Sometimes a little splitting occurs.

Flower stem:

*Length.*—Averages about 71.5 cm, when cut at the tenth node.

*Character.*—Strong, erect and rigid.

*Color.*—199-A/B.

THE FLOWER

Blooming habit: Recurrent, blooming profusely in the Spring, Midseason and Fall blooming periods with a tendency to give few blooms in the Fall.

Size of flower: Medium.

*Diameter.*—Averages about 8.4 cm.

*Depth.*—Averages about 5.8 cm.

Borne: Singly on a long, strong, upright stem.

Shape: When bloom first opens, high-centered. When bloom matures, dome-shaped.

Petalage:

*Number of petals.*—Averages about eighty-seven.

*Arrangement.*—Imbricated.

*Form.*—Fan-shaped with rounded edges with very little serration.

*Texture.*—Leathery.

*Appearance.*—A little satiny.

*Color.*—Both inner and outer petals: Body — 2-C, with striae of Empire Rose, 48-C/D, and sometimes 155-D. Base — Whitish. Reverse side — 2-C with striae of 48-D and sometimes 155-D.

Petaloids:

*Number.*—Less than fourteen.

*Size.*—Smaller than the petals.

*Color.*—The same as the petals.

Flower stem:

*Character.*—Upright with good strength and outwardly curved foliage.

Discoloration after full bloom: Very little.

Persistence: On the plant, the flowers hang on and dry.

Fragrance: Perceptible.

Lasting quality: As a cut flower, at least ten days in vase keeping.

REPRODUCTIVE ORGANS

Stamens:

*Number.*—Varies from ten to twenty-two.

*Arrangement.*—Around the ovary.

*Anthers.*—Size: Less than 4 mm. Color: Yellowish.

*Filaments.*—Color: Yellowish.

Pistils:

*Number.*—Two to four.

*Styles.*—Length: About 1.5 cm. Color: Yellowish.

*Stigma.*—Color: Yellowish.

Character of ovaries: Ribbed.

This carnation cultivar most nearly resembles the variety Londorga (U.S. Plant Pat. No. 5,784). This new carnation cultivar differs from Londorga, however by having considerably more striae in the flower petals and the plant, as a whole, is less vegatative.

We claim:

1. The new and distinctive variety of standard carnation substantially as herein shown and described, particularly characterized by medium sized blooms, the petals of which are of a uniform, clear light yellow base color, longitudinally striated with fine lines of pink and sometimes white, the flowers being produced profusely on strong, upright stems of a tall plant having a vigorous upright and rigid growth habit reaching an average height of about 140 cm.

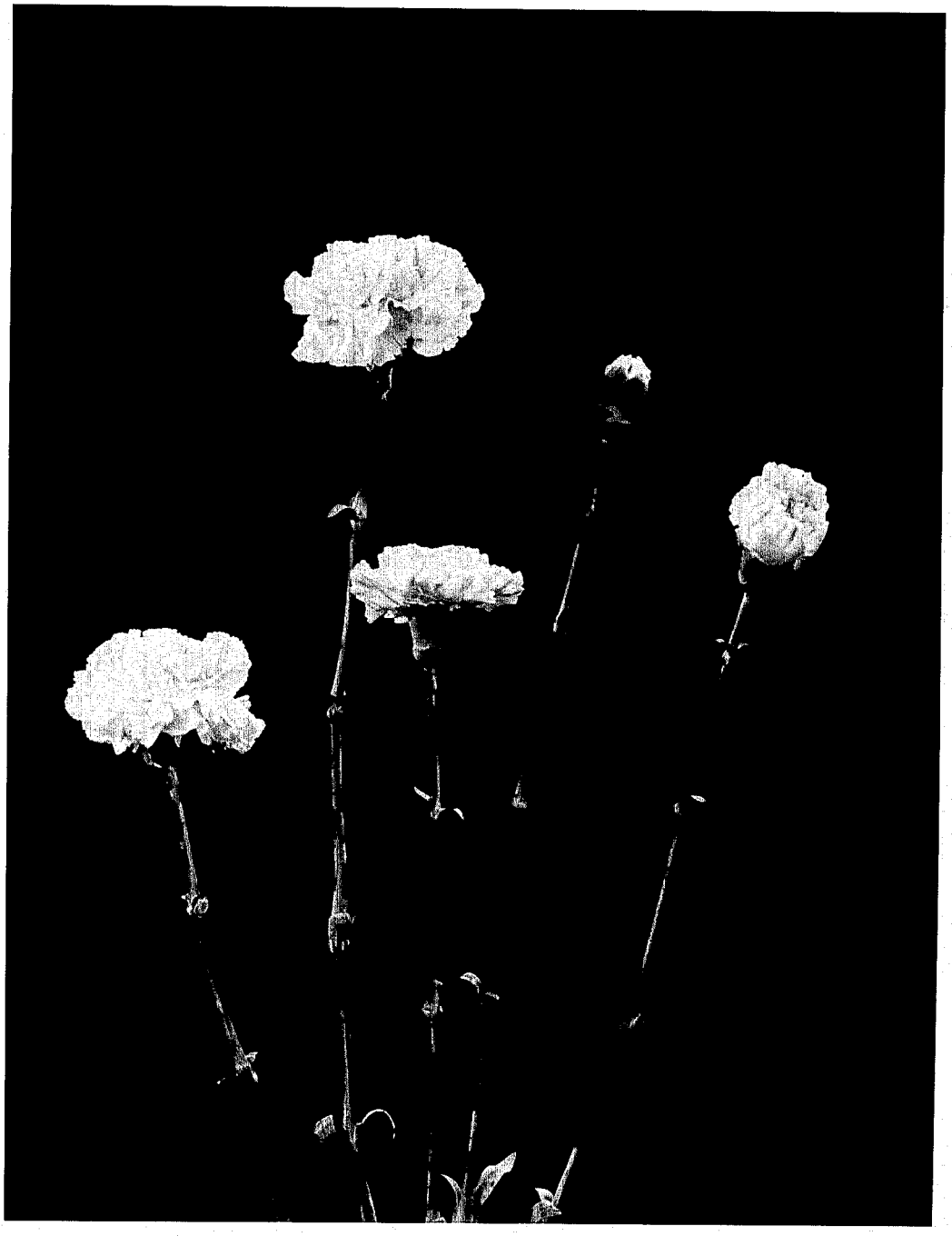

* * * * *